United States Patent [19]

Frantz

[11] 4,299,569
[45] Nov. 10, 1981

[54] ORTHODONTIC BRACKET FOR STRAIGHTENING TEETH

[76] Inventor: Leonard Frantz, 12860 Biscayne Blvd., North Miami, Fla. 33161

[21] Appl. No.: 738,098

[22] Filed: Nov. 2, 1976

Related U.S. Application Data

[63] Continuation-in-part of Ser. No. 665,163, Mar. 8, 1976, abandoned.

[51] Int. Cl.³ ............................................. A61C 7/00
[52] U.S. Cl. ..................................................... 433/8
[58] Field of Search ....................... 32/14 A; 433/8, 9

[56] References Cited

U.S. PATENT DOCUMENTS 2,908,974 10/1959 Stifter ................................. 32/14 A
3,765,091 10/1973 Northcutt ........................... 32/14 A
3,964,165 6/1976 Stahl .................................. 32/14 A Primary Examiner—Robert Peshock
Attorney, Agent, or Firm—Hopgood, Calimafde, Kalil, Blaustein & Judlowe

[57] ABSTRACT

An orthodontic bracket for straightening teeth has a plastic base member for cementing to a tooth with a bracket portion extending outwardly thereof with a slot thereacross. The slot is substantially wholly contained in an elongated metal insert lengthwise thereof molded immovably into said plastic. The slot is rectangular in cross section for receiving a similarly shaped arch wire for controlling the position of the tooth anteroposteriorly, laterally and longitudinally on its long axis.

20 Claims, 9 Drawing Figures

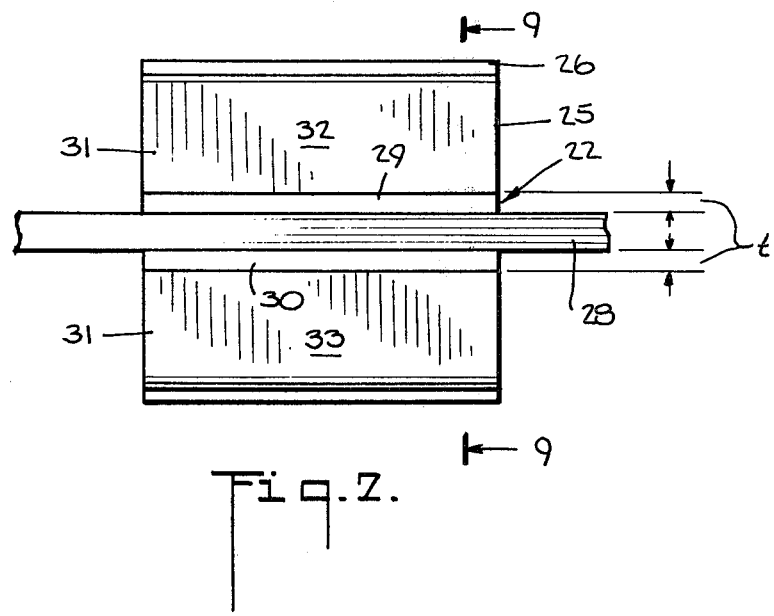
Fig. 7.
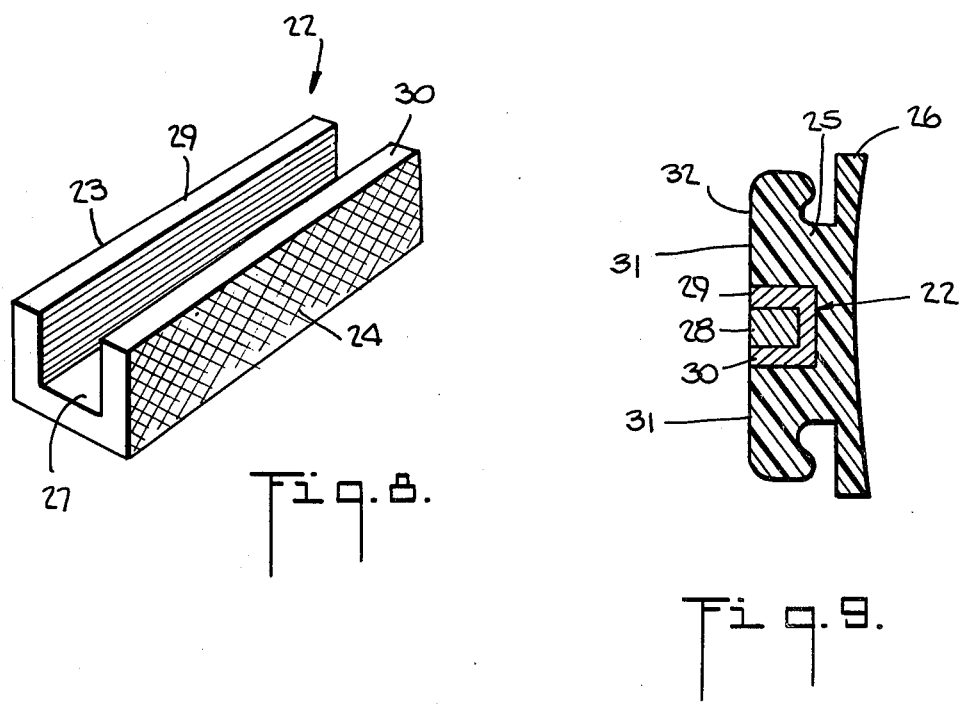
Fig. 8.
Fig. 9.

ORTHODONTIC BRACKET FOR STRAIGHTENING TEETH

This application is a continuation-in-part of application Ser. No. 665,163, filed Mar. 8, 1976 and now abandoned. This invention relates to orthodontic brackets for use in straightening teeth and is directed more particularly to unobtrusive plastic brackets bondable to the teeth and having an arch wire receiving slot of rectangular cross section thereacross.

BACKGROUND OF THE INVENTION

Two developments have in recent years brought on changes in the field of the orthodontist as to the manner of applying brackets to teeth for straightening them. Originally, metal bands were mounted and cemented about a tooth to be straightened. The metal band had attached at its front surface a metal bracket for receiving the arch wire that applied appropriate forces to the tooth in its straightening action. With new and stronger adhesives made available, it became possible to cement the bracket directly to the tooth. With the development of stronger plastics, orthodontists became able to eliminate the metal band and through the use of a clear plastic bracket provide for a more esthetic appearance with greater comfort to the users.

However, it became apparent that exact precision of results were not forthcoming with the use of plastic brackets for the reason that metal arch wires placed in the slotted portions formed in the plastic bracket did not provide the required precision and exactness of tooth movement and there was a loss of proper control of tooth position theretofore achieved by the combined metal brackets mounted on metal bands and use of metal arch wires. The reason for loss of control is due to the fact that plastics do not have the same strength and density of metal. Therefore, plastic brackets cemented on a person's teeth tend to abrade, stretch, give and become distorted as well as possibly fracture under the forces on an arch wire in attempting to straighten teeth orthodontically.

The tendency of the plastic to distort excessively and, in some cases, actually fracture when forces are applied via an arch wire attached thereto, was recognized in U.S. Pat. No. 3,930,311 issued Jan. 6, 1976. In an attempt to overcome said problem, said patent describes the use of a sheet metal stiffening core embedded in the plastic extending essentially normal to the longitudinal axis of the slot in the bracket so as to reinforce the wings projecting on either side thereof. The major portion of the exposed surfaces of the slot remain plastic while only a thin edge of the core is exposed as a narrow band bisecting the walls of the slot.

Unfortunately, the precise positioning of the cores as disclosed in said patent is difficult if not impossible to obtain in practice, and it is extremely difficult, if indeed possible, to mold plastic thereabout. Moreover, the major surface of the slot remains plastic and is still subject to the various deficiencies inherent in the material such as the susceptibility to abrasion, stretching and giving under the forces of the arch wire. An additional disadvantage with the structure described in said patent is that when transparent or translucent plastic is used the metal cores are readily visible in the wings on either side of the slot and detract from the unobtrusive characteristic of otherwise transparent plastic.

BRIEF SUMMARY OF THE INVENTION

It is the intention of the present invention to avoid the disadvantages stated above while retaining the advantages of clear plastic brackets in such manner that the combined advantages of both metal and plastic are retained without loss of esthetic appearance and comfort of the orthodontic bracket to the user. In this connection, a principal object of the present invention is to provide a plastic orthodontic bracket adapted to be cemented directly onto the front surface of the tooth, which bracket has a rectangular slot for receiving a similarly shaped arch wire for precise positioning of the tooth in the three planes of space, namely, the anteroposterior, lateral and longitudinal axes of the tooth.

Another object of the present invention is to provide a plastic bracket for the orthodontic straightening of a tooth with a metallic insert having a rectangular cross-sectioned slot for receiving a similarly shaped arch wire for exact precision fit and control of the tooth position that will result in the tooth becoming straightened.

A further object of the present invention is to provide a plastic bracket having a rectangular base member adapted to be cemented to a tooth to be straightened with a bracket portion extending outwardly of the base member and a slotted portion for receiving a metallic insert along whose axis is a rectangular cross-sectioned slot for receiving a similarly shaped arch wire therein.

In accordance with the present invention, there is provided an orthodontic bracket comprising a base portion with an integral bracket portion extending therefrom, said base portion having a surface for use in adhesively mounting the bracket on the wall of a tooth with the bracket portion extending therefrom, said bracket portion having an exposed face with a rectangularly cross-sectioned slot thereacross for snugly receiving a rectangular arch wire therein, and said base and bracket portions consisting essentially of a visually unobtrusive substantially rigid plastic, characterized in that said slot is substantially wholly contained in an elongated metal insert lengthwise thereof molded immovably into said plastic, said insert having side walls that as seen from said exposed face of said bracket portion have a thickness that is substantially less than the dimension in the same direction of the adjacent areas of said exposed face such that said insert is visually substantially indistinguishable from an installed arch wire when in use, but sufficient to resist fracture of the surrounding plastic by the arch wire and to maintain precision dimensional control of said slot.

The invention will be better understood from a consideration of the following detailed description taken in connection with the accompanying drawings forming a part of this specification, of the presently preferred embodiments thereof, with the understanding, however, that the invention is not confined to any strict conformity with the showing of the drawings but may be charged or modified so long as such changes or modification mark no material departure from the salient features of the invention as expressed in the appended claims.

BRIEF DESCRIPTION OF THE DRAWINGS

In the drawings:

FIG. 7 is a top plan view of a further modified bracket;

FIG. 8 is a perspective view of the metallic insert employed in the bracket of FIG. 7; and FIG. 9 is a cross sectional view taken along the line 9—9 of FIG. 7.

DETAILED DESCRIPTION OF THE PREFERRED EMBODIMENTS

Figure 1:
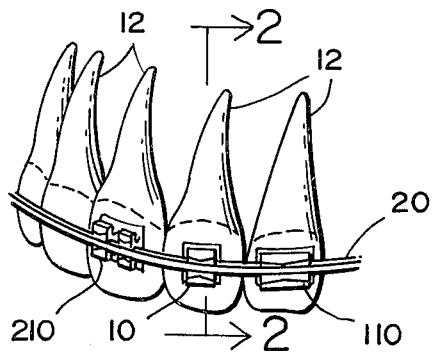
FIG. 1 is a perspective view showing a person's teeth having orthodontic appliances of the present invention applied thereto.

Referring to the drawings wherein like reference numerals are used to designate similar parts throughout the several views, the numeral 10 refers to an orthodontic bracket for straightening teeth constructed in accordance with the invention and consisting of a base plate portion 11 whose rear surface is contoured to fit snugly on teeth 12 and to which the base plate 11 can be cemented. The orthodontic bracket 10 is an integral plastic member made of either clear plastic or tooth colored plastic having substantial rigidity to be able to withstand without giving to the forces of an arch wire 20 as explained in detail hereinafter.

Figure 2:
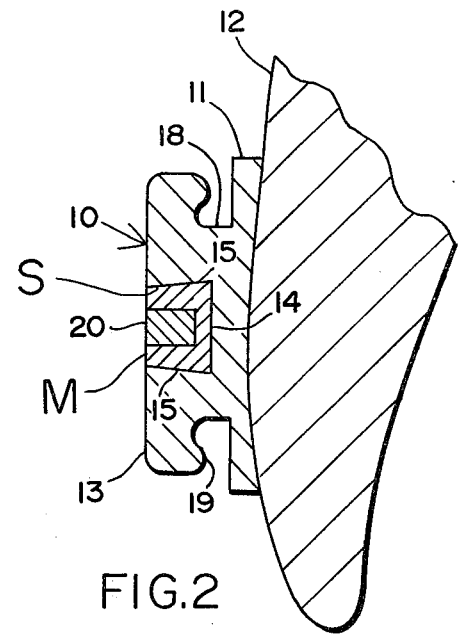
FIG. 2 is a cross sectional view taken along the line 2—2 of FIG. 1.
Figure 3:
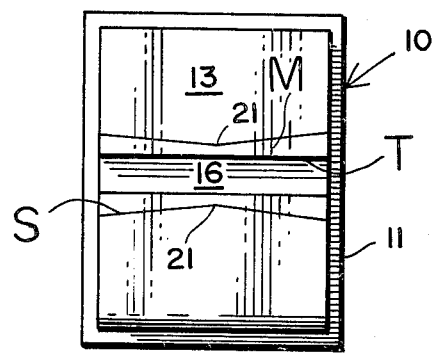
FIG. 3 is a top plan view of the bracket alone.
Figure 4:
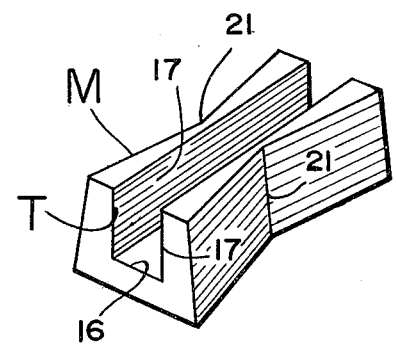
FIG. 4 is a perspective view of a metallic insert.

Extending from the base portion 11 is the bracket portion 13 having a slotted portion -S- extending across the mid-portion of the bracket portion 13. The slotted portion -S- has an open top with a flat base wall 14 and undercut side walls 15 converging in a direction toward each other in two planes, namely, from the inner to the outer edges of the slotted portion -S- as well as in the direction of the mid-portion 21 of the bracket portion 13. As seen in FIG. 2, the slot -S- is of dovetail configuration while as seen in FIG. 3 the taper extending inwardly longitudinally from both ends of the slot produces a narrower medial region for a purpose to be explained hereinafter.

Fitted into the slotted portion -S- at the time of molding of the plastic bracket 10 is a metal insert -M- whose outer surfaces are so shaped as to conform with those of the slotted portion -S-. In fact, the shape of the insert -M- determines the shape of the slotted portion -S- since the bracket 10 is molded directly about the insert -M-. The inner portion of the metallic insert -M- is provided with an open top slot -T- having a rectangular cross section with a rectangular shaped base 16 and rectangular shaped inner side walls 17. The slot -T- is adapted to snugly receive a firmly fitted rectangular shaped arch wire 20. The bracket portion 13 joins the base plate portion 11 in a narrowed portion forming a peripheral slotted portion 18 and an overhang 19 to permit the insertion of wires by the orthodontist to secure the arch wire 20 in the slotted portion -T- of the metallic insert -M-. It will be recognized that the overhang portions 19 form wings and that the slot 18 is provided to receive ligatures of one form or another.

Figure 5:
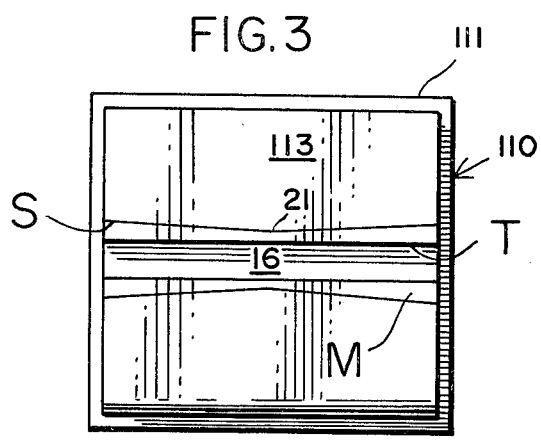
FIG. 5 is a plan view of a modified form of bracket for moderately sized teeth.
Figure 6:
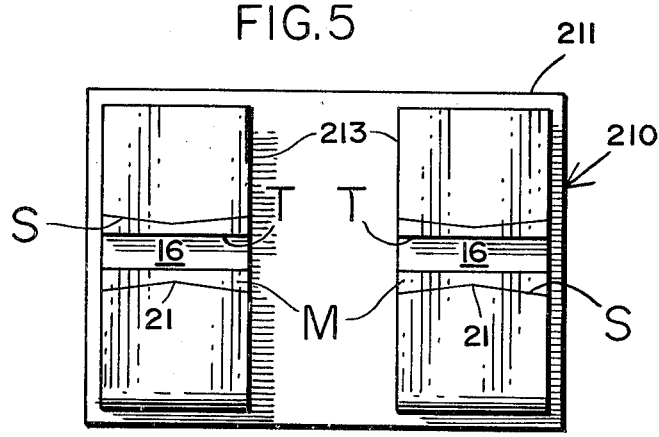
FIG. 6 is a top plan view of another embodiment of the bracket for large teeth.

FIGS. 5 and 6 which show modified forms of bracket 10 are identical in construction except for size of the base plates and bracket portions in order to accommodate teeth of various sizes and shapes. The bracket 10 described hereinabove in detail is adapted to be mounted on the smallest size teeth. The bracket 110 shown in FIG. 5 is provided with a large base plate 111 and a further elongated metallic insert -M-. The bracket 210 which is shown in FIG. 6 and intended for use on the largest of teeth consists of a relatively large base plate 211 on which are a pair of spaced bracket portions 213 having slotted portions -S- in axial alignment formed thereon with a metallic insert -M- molded into each of the slotted portions -S-.

Referring now to FIGS. 7, 8 and 9 there is shown a modified bracket wherein the insert 22 is rectangular in both internal and external cross section and has its exterior side walls 23 and 24 roughened by diamond knurling or the like to permit interaction with the plastic during molding such that displacement of the insert relative to the plastic is resisted.

As seen in FIG. 9, the elongated metal insert 22 has been molded immovably into the plastic of the bracket portion 25 which extends from the base portion 26. The insert 22 has a rectangularly cross-sectioned slot 27 lengthwise thereof for snugly receiving an arch wire 28. As best seen in FIGS. 7 and 9, the exposed edges 29 and 30 of the side walls of the insert 22 as viewed looking toward the exposed vace 31 of the bracket portion have a thickness (dimension t in FIG. 7) that is substantially less than the dimension in the same direction of the adjacent areas 32 and 33 of said exposed face 31 such that the insert 22 is visually substantially indistinguishable from the installed arch wire 28. It has been found that a relatively thin walled insert is sufficient to resist fracture of the surrounding plastic by the arch wire 28 and to maintain precision dimensional control of the slot which is wholly contained therein, namely the slot 27. It should be apparent that this visual advantage and dimensional control are also attained by the brackets described with reference to FIGS. 1 through 6.

It should be understood that other constructional arrangements besides knurling as used in the embodiment of FIGS. 7 to 9 and dovetailing as used in the embodiments of FIGS. 1 through 6 may be employed to ensure that the metal insert remains immovable within the plastic.

In the normal use of the brackets described above, the appropriate size bracket is selected for the tooth on which it is to be cemented. It should be understood that the various sizes and configurations shown in FIGS. 3, 5 and 6 may all be modified in the manner illustrated in the bracket shown in FIGS. 7, 8 and 9. When the brackets are mounted and aligned on the teeth, the arch wire is inserted edgewise in the respective slots and secured therein by appropriate ligatures (not shown) in a manner causing proper forces to be created that effect a straightening action on the teeth. Since the arch wire 20 or 28 and the insert -M- or 22, in which it is received, are of metal and of fitted rectangular shapes, the insert will transmit all of the forces being applied by the arch wire to the tooth in strength and direction with exact precision. As a result, the teeth will be properly straightened and the time required for effecting same is reduced to a minimum.

It should be observed that in the embodiment of FIG. 7 the length of the metal insert 22 and the width of the bracket portion 25 coincide with the width of the base plate or portion 26 whereas the base plates 10, 110 and 210 in the embodiments of FIGS. 3, 5 and 6 project beyond the bracket portions. The converse relationship is also permissible in that the projection of the base plate in the embodiment of FIGS. 3, 5 and 6 may be eliminated while the base plate of the embodiment of FIG. 7 may be increased in width. Moreover, the base plate need not be rectangular but may take any other suitable outline adaptable to the configuration of the teeth.

In order to afford a better understanding of the relative dimensions contemplated by the present invention, a bracket such as that shown in FIG. 7 may have a square exposed face 31 measuring ⅛ inch on each side while the width of the walls of the metal insert 22 at the surface of the exposed face, namely, dimension t may be only about 0.011 inches and the width of the slot -T- or 27 may be about 0.018 inches.

What is claimed is:

1. An orthodontic bracket comprising a base porrtion with an integral bracket portion extending therefrom, said base portion having a surface for use in adhesively mounting the bracket on the wall of a tooth with the bracket portion extending therefrom, said bracket portion having an exposed face with a rectangularly cross-sectioned slot thereacross for snugly receiving a rectangular arch wire therein, and said base and bracket portions consisting essentially of a visually unobtrusive substantially rigid plastic, characterized in that said slot is substantially wholly contained in an elongated metal insert lengthwise thereof molded immovably into said plastic, said insert having side walls that as seen from said exposed face of said bracket portion have a thickness that is substantially less than the dimension in the same direction of the adjacent areas of said exposed face such that said insert is visually substantially indistinguishable from an installed arch wire when in use, but sufficient to resist fracture of the surrounding plastic by the arch wire and to maintain precision dimensional control of said slot.

2. An orthodontic bracket according to claim 1, characterized in that said insert is trapezoidal in external cross section and dovetailed into said plastic.

3. An orthodontic bracket according to claim 2, characterized in that said insert has its exterior side walls tapered inwardly longitudinally from both ends producing a narrower medial region for resisting endwise displacement in said plastic.

4. An orthodontic bracket according to claim 2, characterized in that the exterior side walls of said insert are roughened to resist displacement in said plastic.

5. An orthodontic bracket according to claim 1, characterized in that said insert has roughened exterior side walls for resisting displacement in said plastic.

6. An orthodontic bracket according to claim 1, characterized in that said insert is provided with means for affording interlocking engagement with said plastic to resist displacement of said insert in said plastic.

7. An orthodontic bracket according to claim 1, wherein said bracket portion includes wings for ligating formed from said plastic.

8. An orthodontic bracket assembly comprising: a hard, non-elastomeric, non-metallic bracket having an opening therein for receiving an arch wire, or the like; and a rigid, substantially non-flexible liner on at least a portion of the surface of said non-metallic bracket defining said opening for protecting said non-metallic bracket from damage due to forces applied by an arch wire, or the like, received therein, said liner being fabricated of a material harder than the material of said bracket.

9. An assembly according to claim 8 wherein said liner is fabricated from metal.

10. An assembly according to claim 9 wherein said bracket is fabricated from hard, non-elastomeric plastic material.

11. An assembly according to claim 8 wherein said bracket is fabricated from hard, non-elastomeric plastic material.

12. An assembly according to claim 11 wherein said liner is non-flexible.

13. An assembly according to claim 8 wherein said liner includes means for positively engaging said opening of said bracket.

14. An assembly according to claim 13 wherein said liner has a generally trapezoidal outer periphery in cross section and said opening of said bracket has a generally trapezoidal shape which matingly receives said liner.

15. An assembly according to claim 13 wherein the outer surface of said liner is irregularly shaped.

16. An assembly according to claim 8 wherein said liner is generally U-shaped.

17. An assembly according to claim 8 wherein said liner substantially covers the complete surface portion of said bracket which defines said opening.

18. An assembly according to claim 17 wherein said liner includes means for positively engaging said opening of said bracket.

19. An assembly according to claim 18 wherein said liner has a generally trapezoidal outer periphery in cross section and said opening of said bracket has a generally trapezoidal shape which matingly receives said liner.

20. An assembly according to claim 18 wherein the outer surface of said liner is irregularly shaped.

* * * * *